US 6,657,714 B2

(12) United States Patent
Almogy et al.

(10) Patent No.: US 6,657,714 B2
(45) Date of Patent: Dec. 2, 2003

(54) DEFECT DETECTION WITH ENHANCED DYNAMIC RANGE

(75) Inventors: Gilad Almogy, Givataim (IL); Boris Goldberg, Ashdod (IL); Ron Naftali, Shoam (IL)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 10/050,889

(22) Filed: Jan. 15, 2002

(65) Prior Publication Data

US 2003/0058433 A1 Mar. 27, 2003

Related U.S. Application Data

(60) Provisional application No. 60/324,341, filed on Sep. 24, 2001.

(51) Int. Cl.[7] ............................................. G01N 21/00
(52) U.S. Cl. ................................. 356/237.3; 356/237.5
(58) Field of Search ........................ 356/237.1–237.6, 356/364, 236, 394; 250/559.01, 559.09, 559.11, 559.41, 562, 572

(56) References Cited

U.S. PATENT DOCUMENTS

| | | | |
|---|---|---|---|
| 4,647,975 A | | 3/1987 | Alston et al. |
| 4,889,998 A | * | 12/1989 | Hayano et al. .......... 250/559.41 |
| 4,965,454 A | * | 10/1990 | Yamauchi et al. .......... 250/372 |
| 5,072,128 A | * | 12/1991 | Hayano et al. .......... 250/559.18 |
| 5,159,408 A | * | 10/1992 | Waldenmaier et al. ...... 356/485 |
| 5,159,412 A | * | 10/1992 | Willenborg et al. ......... 356/445 |
| 5,177,559 A | | 1/1993 | Batchelder et al. |
| 5,276,498 A | | 1/1994 | Galbraith et al. |
| 5,506,676 A | * | 4/1996 | Hendler et al. .......... 356/237.1 |
| 5,699,447 A | | 12/1997 | Alumot et al. |
| 5,777,729 A | * | 7/1998 | Aiyer et al. ............. 356/237.1 |
| 5,790,247 A | * | 8/1998 | Henley et al. ........... 356/237.1 |
| 5,929,994 A | * | 7/1999 | Lee et al. .................... 356/364 |
| 5,940,175 A | * | 8/1999 | Sun .......................... 356/237.3 |
| 5,982,921 A | | 11/1999 | Alumot et al. |
| 6,002,122 A | | 12/1999 | Wolf |
| 6,081,325 A | * | 6/2000 | Leslie et al. ............. 356/237.2 |
| 6,178,257 B1 | | 1/2001 | Alumot et al. |
| 6,256,093 B1 | * | 7/2001 | Ravid et al. ............. 356/237.2 |
| 6,366,352 B1 | * | 4/2002 | Goldberg et al. ........ 356/237.2 |

FOREIGN PATENT DOCUMENTS

WO        WO 90/01845        2/1990

OTHER PUBLICATIONS

U.S. patent application No.: 09/595,902, entitled: "Optical Inspection Method and Apparatus Utilizing a Collection Angle Design".

* cited by examiner

*Primary Examiner*—Frank G. Font
*Assistant Examiner*—Sang H. Nguyen
(74) *Attorney, Agent, or Firm*—Blakely Sokoloff Taylor & Zafman

(57) ABSTRACT

Apparatus for optical inspection includes a source of optical radiation, which is adapted to scan a spot of the radiation over a sample, whereby the radiation is scattered from the spot. A detection system includes at least first and second detectors optically coupled to receive the scattered radiation and to generate respective first and second outputs responsive thereto, the detection system being configured so that the first detector detects variations in the scattered radiation with a greater sensitivity than the second detector, while the second detector saturates at a higher intensity of the scattered radiation than does the first detector. A signal processor is coupled to receive the first and second outputs and to determine, responsive to the outputs, locations of defects on the sample.

44 Claims, 4 Drawing Sheets

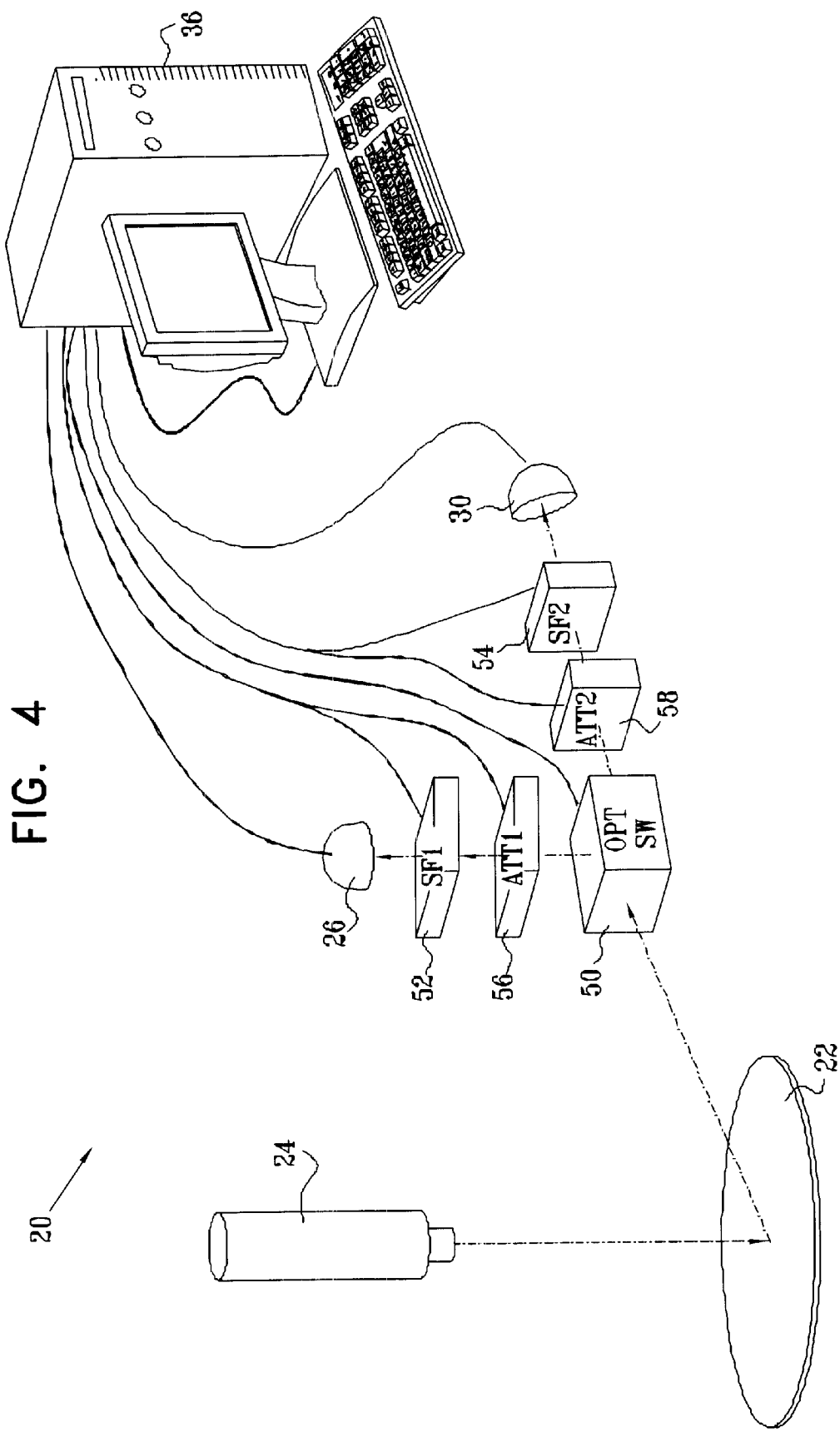

DEFECT DETECTION WITH ENHANCED DYNAMIC RANGE

CROSS-REFERENCE TO RELATED APPLICATION

This application claims the benefit of U.S. Provisional Patent Application No. 60/324,341, entitled "System and Method for Defect Detection," filed Sep. 24, 2001, which is incorporated herein by reference.

FIELD OF THE INVENTION

The present invention relates generally to optical inspection systems, and specifically to methods and systems for detecting defects on substrates.

BACKGROUND OF THE INVENTION

Dark-field systems are well known in the art of optical inspection, particularly for detection of defects on substrates such as semiconductor wafers. Optical signals generated in dark-field inspection are typically characterized by very high dynamic range. The signal depends both on the reflectance of the material in the spot under inspection (as a function of the complex index of refraction) and on spatial variations within the spot. In bright-field systems, the reflectance usually dominates, and the resulting variations in the collected signal are generally no more than about two orders of magnitude. In the case of dark-field detection, however, smooth surfaces lead to almost no collection signal, while surfaces with protruding features may scatter many orders of magnitude more.

Patterned wafers used in producing advanced integrated circuits typically contain regions whose dark-field scattering signals may vary by six orders of magnitude or more. Examples of this phenomenon include scattering variations between the following types of regions:

Scribe lines scatter light differently from pattern regions.
Memory blocks scatter differently from their associated I/O circuitry.
Cache memory of a microprocessor unit scatters differently from the logic area.
A given memory region may have a pitch that generates a strong diffraction lobe toward a detector used to collect the scattered radiation, while the lobes of another region with a different pitch may escape detection.
Bare patches (down to several microns in size) scatter far less than adjoining regions of dense pattern.

The sensitivity of an inspection tool can be optimized for these different regions by controlling both signal acquisition (e.g., laser power and detector gain) and signal processing parameters. It is very difficult, however, to vary the acquisition parameters on the fly, in the process of scanning a single wafer, without reducing the inspection throughput, because the scan speed must generally be reduced in order to avoid artifacts due to rapid changes in the acquisition parameters. Furthermore, defining different regions on the wafer for signal acquisition and processing is a cumbersome task. In the particular case of bare patches (which may be as little as several microns in size, corresponding to a few pixels of the inspection system) between regions of dense pattern, it is impractical to program the inspection system to change its acquisition and processing parameters per region. Although the inspection system may, in principle, be able to adaptively learn the signal processing parameters, it is nearly impossible for the acquisition parameters to adapt within the time span of several pixels. In typical operation of a modern inspection system, this time span is typically no more than tens to hundreds of nanoseconds.

There is therefore a need, particularly in dark-field inspection, for detection systems with a very large dynamic range, in order to collect meaningful signals from both the very dark and the bright areas of the substrate being inspected without on-the-fly adjustment. Achieving a dynamic range greater than 10 or 12 bits (1:1024 or 1:4096) is very difficult, however, with detection systems operating at high data rates (tens to hundreds of mega-samples per second). The dynamic range of the detector itself is limited by the ratio of the saturation power to the minimal detectable signal, typically governed by the noise level of the detector and amplification circuitry. A further limitation is imposed by the restricted bit range of fast analog-to-digital converters.

One possible solution to this problem is to apply non-linear amplification to the output signal from the detector, in order to emphasize the low-amplitude signal range. An approach of this sort is described by Wolf in U.S. Pat. No. 6,002,122, whose disclosure is incorporated herein by reference. The dark-field detector output in this case is processed by a logarithmic amplifier and gain correction mechanism. Although this approach may provide improved visibility of defects in a dark-field image of a substrate, it does nothing to address the fundamental limitation of the dynamic range of the detection system.

Multiple-exposure imaging systems are known in the art. For example, U.S. Pat. No. 4,647,975, to Alston et al., whose disclosure is incorporated herein by reference, describes an electronic imaging camera with expanded dynamic exposure range, based on implementing two succeeding exposure intervals with different exposure parameters. A combined image is then constructed by choosing between the electronic information signals sensed during the two exposure intervals. Typically, the camera is used to combine one exposure of a scene taken with ambient light and another taken under flash illumination. PCT patent publication WO 90/01845, to Ginosar et al., whose disclosure is also incorporated herein by reference, describes image pickup apparatus including multiple image sensors receiving an image at various exposure levels. The sensor outputs are combined to create a single image with widened dynamic range.

SUMMARY OF THE INVENTION

It is an object of some aspects of the present invention to provide improved systems and methods for optical inspection, and particularly for detecting defects on a substrate.

It is a further object of some aspects of the present invention to provide dark-field detection systems having enhanced dynamic range.

In preferred embodiments of the present invention, a dark-field optical detection system comprises an illumination source, such as a laser, which scans a substrate under inspection, and two or more detectors for capturing light scattered from the substrate. Preferably, one of the detectors is optimized for high sensitivity, while another is designed to have a high saturation level, typically at the expense of its sensitivity. The light scattered from each point on the substrate is split among the detectors, wherein the respective portions of the radiation directed to the different detectors are not necessarily equal. Preferably, the light is split among the detectors in a consistent manner that is independent of polarization and angle, using a common integrating sphere, for example, to feed all the detectors.

The output of each of the detectors is sampled by its own processing channel. The output of the high-sensitivity channel provides information regarding defects on the substrate in areas of low scattered intensity, while that of the high-saturation channel provides information regarding areas of high scattered intensity. The use of multiple parallel detectors thus allows shot-noise-limited detection in areas with very little available light, without losing the signal due to saturation in bright areas. In this manner, defects on the substrate are detected with far greater dynamic range than can be achieved using single-detector systems, as are known in the art.

In some preferred embodiments of the present invention, spatial filtering is applied to the light scattered from the substrate before the light impinges on the detectors. A key purpose of such filtering is to eliminate constructive interference lobes at certain angles due to repetitive patterns on the substrate, as well as blocking reflections from other bright features on the substrate. Such spatial filtering improves the sensitivity of the detectors to weak scattering signals from local defects. In some of these preferred embodiments, a single spatial filter is used to filter the scattered light that is collected by all the detectors. In other preferred embodiments, at least two of the detectors have their own, separate spatial filters. In this manner, a different filtering characteristic can be applied to the weaker scattered light impinging on the high-sensitivity detector from that applied to the strong scattered light impinging on the high-saturation detector.

Although the preferred embodiments described herein relate to dark-field detection of defects on a substrate, typically a semiconductor wafer, the principles of the present invention are similarly applicable to other sorts of scattering measurements and other detection schemes used in optical inspection of samples of various types.

There is therefore provided, in accordance with a preferred embodiment of the present invention, apparatus for optical inspection, including:

a source of optical radiation, which is adapted to scan a spot of the radiation over a sample, whereby the radiation is scattered from the spot;

a detection system, including at least first and second detectors optically coupled to receive the scattered radiation and to generate respective first and second outputs responsive thereto, the detection system being configured so that the first detector detects variations in the scattered radiation with a greater sensitivity than the second detector, while the second detector saturates at a higher intensity of the scattered radiation than does the first detector; and a signal processor, coupled to receive the first and second outputs and to determine, responsive to the outputs, locations of defects on the sample.

Preferably, the first and second detectors have respective first and second dynamic ranges, and the signal processor is adapted to process the first and second outputs so as to generate an combined output having a third dynamic range, greater than the first and second dynamic ranges, for use in determining the locations of the defects. In a preferred embodiment, the signal processor is adapted to generate the combined output as a weighted sum of the first and second outputs In another preferred embodiment, the signal processor is adapted to generate the combined output by selecting, at each point as the spot is scanned over the sample, a value of one of the first and second outputs. In still another preferred embodiment, the detection system includes an optical switch, which is adapted to direct the scattered radiation toward either of the first and second detectors in turn, and the signal processor is coupled to drive the switch so as to select, at each point as the spot is scanned over the sample, one of the detectors to which the scattered radiation is to be directed. Typically, the first and second detectors are characterized by respective gains, which are preferably selected so that the sensitivity of the combined output is shot-noise limited.

In yet another preferred embodiment, the signal processor is coupled to process each of the first and second outputs to generate respective first and second defect maps, and to combine the first and second defect maps to determine the locations of the defects on the sample.

Preferably, the first and second detectors are configured to generate the first and second outputs with respective first and second gains, relative to the intensity of the scattered radiation incident thereon, and wherein the first gain is substantially greater than the second gain. In a preferred embodiment, the first detector includes one of a photomultiplier tube and an avalanche photodiode, while the second detector includes a PIN photodiode.

In a preferred embodiment, the detection system includes a beamsplitter, which is positioned to split the scattered radiation between the first and second detectors. Preferably, the beamsplitter is configured to direct a greater portion of the scattered radiation toward the first detector than toward the second detector.

In another preferred embodiment, the detection system includes a diffraction grating, which is positioned to intercept the scattered radiation and to diffract one order of the scattered radiation toward the first detector, and another order of the scattered radiation toward the second detector.

Preferably, the detection system includes an optical element that is adapted to divide the scattered radiation between the first and second detectors in a manner that is substantially independent of a scattering angle and a polarization of the scattered radiation. In a preferred embodiment, the optical element includes an integrating sphere, having an entrance port that is coupled to receive the scattered radiation, and first and second exit ports that are coupled to convey the scattered radiation to the first and second detectors, respectively.

Preferably, the detection system includes at least one spatial filter, which is configured to block a portion of the scattered radiation from reaching the first and second detectors, so as to facilitate detection of the radiation that is scattered from the defects. In a preferred embodiment, the at least one spatial filter includes first and second spatial filters, which are respectively positioned so that the first spatial filter filters the scattered radiation reaching the first detector, while the second spatial filter filters the scattered radiation reaching the second detector. Preferably, the signal processor is coupled to independently control each of the first and second spatial filters, so as to alter the portion of the scattered radiation that is blocked by each of the spatial filters.

Optionally, the detection includes at least one attenuator, which is controllable so as to adjust an intensity of the scattered radiation that reaches at least one of the first and second detectors.

In a preferred embodiment, the apparatus includes a third detector, optically coupled to receive the scattered radiation and to generate a third output responsive thereto, wherein the sensitivity of the third detector is intermediate the sensitivity of the first and second detectors, and wherein the signal processor is coupled to receive the third output and to determine the locations of the defects responsive to the third output, together with the first and second outputs.

Typically, the optical radiation includes coherent radiation, and the detection system is configured so that the detectors receive the scattered radiation in a dark-field mode. In a preferred embodiment, the sample includes a semiconductor wafer on which a pattern is formed, and the signal processor is adapted to map the locations of the defects in the pattern.

There is also provided, in accordance with a preferred embodiment of the present invention, an integrating sphere, including:

an inlet port, adapted to receive radiation;

a spherical body, having an internal surface that is adapted to diffusely reflect the radiation received through the inlet port; and first and second output ports, adapted to convey the radiation from within the spherical body to first and second detectors, coupled respectively to the ports, the first port having a substantially greater diameter than the second port, whereby a substantially greater portion of the radiation is conveyed to the first detector than to the second detector.

There is additionally provided, in accordance with a preferred embodiment of the present invention, a method for optical inspection, including:

scanning a spot of the radiation over a sample, whereby the radiation is scattered from the spot;

configuring at least first and second detectors so that the first detector detects variations in the scattered radiation with a greater sensitivity than the second detector, while the second detector saturates at a higher intensity of the scattered radiation than does the first detector;

detecting the scattered radiation using at least the first and second detectors so as to generate respective first and second outputs responsive thereto; and processing at least the first and second outputs to determine locations of defects on the sample.

There is further provided, in accordance with a preferred embodiment of the present invention, a method for processing radiation, including:

collecting the radiation in an integrating sphere; and coupling first and second detectors to respective first and second output ports of the integrating sphere, the first port having a substantially greater diameter than the second port, whereby a substantially greater portion of the radiation is conveyed to the first detector than to the second detector.

The present invention will be more fully understood from the following detailed description of the preferred embodiments thereof, taken together with the drawings in which:

BRIEF DESCRIPTION OF THE DRAWINGS

FIGS. 1–4 are schematic, pictorial illustrations of systems for detecting defects on a substrate, in accordance with preferred embodiments of the present invention.

DETAILED DESCRIPTION OF PREFERRED EMBODIMENTS

Figure 1:
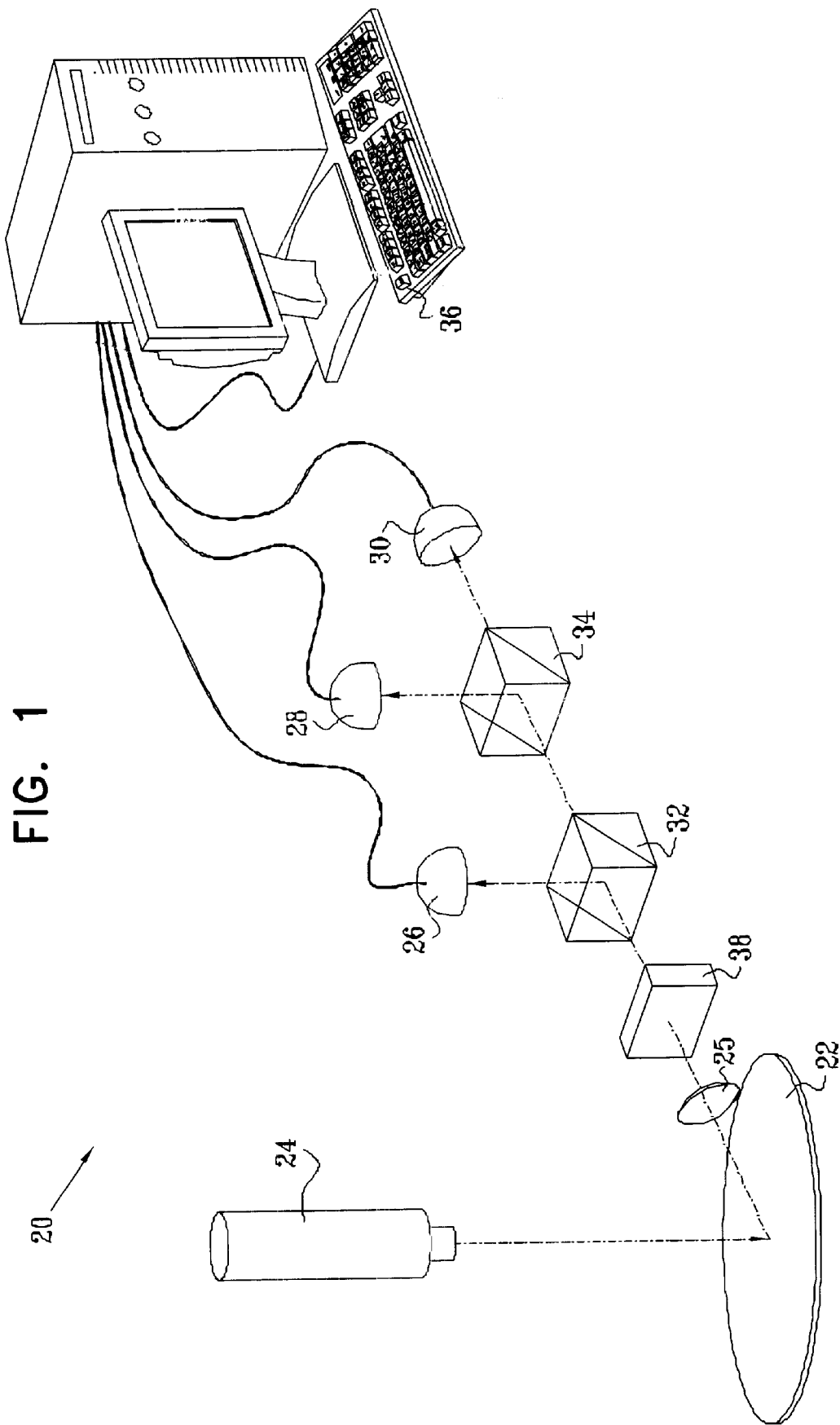

FIG. 1 is a schematic, pictorial illustration of a system 20 for detecting detects on a substrate 22, in accordance with a preferred embodiment of the present invention. Typically, substrate 22 comprises a semiconductor wafer, which is irradiated by a laser source 24 with a beam of coherent light. The beam is scanned over the surface of the substrate, using methods of scanning known in the art. An objective lens 25 collects light scattered from substrate 22, and directs the light toward detectors 26, 28 and 30. Source 24 and lens 25 are preferably arranged in a dark-field configuration, so that the detectors receive only the scattered light, and not reflections of source illumination. In the configuration pictured in the figures, source 24 illuminates substrate 22 in a generally normal direction, while lens 25 collects the scattered light at a low angle. Alternative configurations of illumination and detection may also be used, as will be apparent to those skilled in the art.

A spatial filter 38 is preferably placed in the Fourier plane of lens 25 in order to filter out unwanted angular components of the light scattered from substrate 22. When the substrate contains regularly-repeating structures (as are characteristic of patterned semiconductor wafers, for example), scattering of coherent light from these structures generates constructive interference lobes along well-defined directions. Filter 38 blocks the interference lobes in the Fourier plane, thus facilitating the detection of defects and pattern irregularities on the substrate. Filter 38 may implement any suitable method of spatial filtering that is known in the art. For example, U.S. Pat. No. 5,177,559, to Batchelder et al., whose disclosure is incorporated herein by reference, describes a dark-field imaging system for inspecting repetitively-patterned integrated circuits, using an opaque spatial filter to attenuate spatial frequency components corresponding to the wafer pattern. U.S. Pat. No. 5,276,498, to Galbraith et al., whose disclosure is also incorporated herein by reference, describes a system for performing dark-field surface inspection using a scanned, focused laser beam and an adaptive spatial filter consisting of a liquid crystal light valve array.

As another example, U.S. patent application Ser. No. 09/595,902, to Milshtein et al., which is assigned to the assignee of the present patent application and whose disclosure is incorporated herein by reference, describes a spatial filtering system using a set of masks produced in chrome on a transparent substrate and positioned using a combination of filter wheel and fine translation motors. This patent application also describes a method for a priori determination of the optimal filter configuration by analyzing a high-resolution two-dimensional image of the wafer plane, in combination with the known properties of the materials and three-dimensional configuration of the substrate. Reflective spatial filters may also be used, as described in another U.S. patent application Ser. No. 10/050,890 entitled "Patterned Wafer Inspection Using Spatial Filtering," filed Jan. 15, 2002, which is likewise assigned to the assignee of the present patent application and whose disclosure is incorporated herein by reference. This application also describes a method that can be used to determine the spatial filtering pattern to be applied by filter 38, based on capturing and analyzing an image of the Fourier plane of lens 25 in real time.

Whereas the embodiment shown in FIG. 1 uses a single spatial filter 38 to filter the scattered light that impinges on all of detectors 26, 28 and 30, it is also possible to use a separate filter for each of the individual detectors. An embodiment of this sort is shown in FIG. 4.

A first beamsplitter 32 splits off a portion of the scattered light collected by lens 25 and directs this portion toward detector 26. The light transmitted through the first beamsplitter is split by a second beamsplitter 34 between detectors 28 and 30. The three detectors are used in combination to detect scattering due to defects on substrate 22 with enhanced dynamic range, as described in detail hereinbelow.

Optionally, the methods described herein may be extended to use a greater number of beamsplitters and detectors, depending on the particular illumination and detection conditions in system 20. Alternatively, only beamsplitter 32 and detectors 26 and 30 are used, while beamsplitter 34 and detector 28 are eliminated. For the sake of simplicity, the description below relates explicitly only to this latter configuration, using two detectors and a single beamsplitter. The modifications needed to apply the ideas described below to the case of three or more detectors will be apparent to those skilled in the art.

Preferably, one of the detectors (say detector 26) is configured to receive strong scattered signals, and therefore has a high saturation level, while the other detector (say detector 30) is configured to receive weak scattered signals, with high sensitivity. (If detector 28 is also used, it can be configured, for example, to receive the scattered signals in an intermediate range between the other two detectors.) When the optical signal is weak, it may be below the minimum detectable signal limit of detector 26, but detector 30 can still achieve good signal/noise performance. When the optical signal is strong, detector 30 may saturate, but detector 26 detects the signal with good signal/noise ratio.

The outputs of detectors 26 and 30 are receive by a signal processor 36, typically a computer with suitable front-end analog and digital processing circuits (not shown). Processor 36 analyzes the detector signals to detect and classify defects on substrate 22. An exemplary method for defect detection is described by Alumot et al., in U.S. Pat. Nos. 5,699,447, 5,982,921 and 6,178,257, whose disclosures are incorporated herein by reference. In addition, Ravid et al. describe a useful method of fault classification in U.S. Pat. No. 6,256,093, whose disclosure is likewise incorporated herein by reference. For the purposes of defect detection and classification, processor 36 may analyze the output signals from detectors 26 and 30 individually, or it may alternatively combine the detector outputs to generate, effectively, a single enhanced signal for analysis. Methods for combining and processing the detector signals are described in greater detail hereinbelow.

Ravid et al. use multiple dark-field sensors, spaced apart around a spot on a wafer illuminated by a laser, to capture light scattered in different directions. The sensor outputs are combined and compared in order to detect and classify defects into distinct defect types. Ravid et al. do not suggest, however, that their multiple sensors might be used at different sensitivity levels, to enhance the dynamic range of defect detection as taught by the present invention. On the other hand, multi-detector assemblies, in accordance with preferred embodiments of the present invention, may be deployed at multiple azimuthal positions in system 20 in order to implement the detection scheme of Ravid et al., with the added benefit of enhanced dynamic range.

The splitting ratio of beamsplitter 32 is defined as a function of the required dynamic range, the noise sources in system 20 and the available analog-to-digital converters. In one embodiment, beamsplitter 32 divides the optical signal scattered from substrate 22 equally between the two detectors. Detector 26 is preferably of a type having a high saturation level, for example, a silicon PIN photodiode, such as those available from UDT (El Segundo, Calif.). Detector 30 preferably comprises a high-sensitivity detector, for example, a photomultiplier tube (PMT), such as those available from Hamamatsu (Hamamatsu City, Japan), or an avalanche photodiode (APD), as is available from Advanced Photonics (Santa-Barbara, Calif.). Detector 30 preferably has a "damage control" mechanism (not shown), so that it can recover rapidly and without damage from high light levels (or intensities). "Damage control" of this sort can be implemented by limiting the supply current to the detector, using a nonlinear or saturable detector gain characteristic, or placing a nonlinear optical absorber between beamsplitter 32 and detector 30.

In other embodiments, beamsplitter 32 splits the light unequally between the detectors. Typically, a greater portion of the light is directed to the high-sensitivity detector, so that it can maintain an adequate signal/noise ratio even when the scattered light is weak. For example, if beamsplitter 32 divides the scattered light between detectors 26 and 30 with an intensity ratio of 1:10, the dynamic range of system 20 will effectively be increased by 900% over the characteristic dynamic range of either of the detectors taken alone.

As noted above, processor 36 may process the signals output by detectors 26 and 30 in a number of alternative ways:

Selection—For each point on substrate 22, the output of high-sensitivity detector 30 is selected for use as the output signal if it is not saturated, while the output of detector 26 is used otherwise. The selection can be made either in software or by a high-speed analog or digital switching circuit (not shown) in processor 36.

Parallel—The signal output by each of the detectors is processed individually to generate a defect map of substrate 22. The defect map based on the output of detector 26 typically shows only defects that scatter strongly, while that based on the output of detector 30 shows defects that scatter weakly, with saturation in the area of bright defects. The maps are combined to give a single map output with wide dynamic range.

Reconstruction—A weighted sum of the outputs of detectors 26 and 30 is calculated, resulting effectively in a single combined detector signal with enhanced dynamic range.

An exemplary method for reconstruction of an output signal with wide dynamic range will now be described. For this purpose, we define the following terms:

$S_{in}$—total optical signal in arbitrary units r—part of signal going to detector 30 (high sensitivity)

1-r—part of signal going to detector 26 (high saturation)

G—ratio between gain of detectors 30 and 26

S1—digitized signal from detector 30

S2—digitized signal from detector 26

$n_1$, $n_2$—number of digitization bits for detector 30 and detector 26, respectively $w_1(S1,S2)$—weighting function for the high-sensitivity signal (S1)

$w_2(S1,S2)$—weighting function for the high-saturation signal (S2)

$S_{out}$—digital output signal ($n_{out}$ bits)

Typically, the weighting values $w_1$ and $w_2$ depend on the gain difference (G), the optical power distribution (r), the number of bits in S1 ($n_1$) and S2 ($n_2$), the system noise characteristics, and the number of output bits required ($n_{out}$). The output signal $S_{out}$ is preferably generated using a look-up table (LUT), to add the two signals S1 and S2 with the correct weighting values:

$$S_{out} = S1 \cdot w_1(S1,S2) + S2 \cdot G \cdot w_2(S1,S2) \tag{1}$$

(This operation also compresses the output signal to the required number of output bits for processing $n_{out}$.) Typically, when the high-sensitivity signal S1 is very low, $w_1(S1,S2)=1$ and $w_2(S1,S2)=0$. On the other hand, when S1 is in saturation, $w_1(S1,S2)=0$ and $w_2(S1,S2)=1$. In between these extremes, $w_1(S1,S2)$ is preferably monotonically decreasing in S1, while $w_2(S1,S2)$ is monotonically increasing. Setting $w_1$ and $w_2$ to vary between the values 0 and 1 as step functions of (S1,S2) is equivalent to the "selection" method of combining the signals S1 and S2 mentioned above. For simplicity, equation (1) assumes zero offset for both detector channels, but the equation may be modified to deal with offset, as well.

The actual dynamic range enhancement that is achieved in system 20 depends, inter alia, on the sources of noise in the system. Let us assume a shot-noise mechanism (which is proportional to the square-root of the signal), with the noise equivalent signal being the least significant bit in the output of the high-sensitivity detector. The maximal gain factor (G) we can choose without having the digitization quantum become more than the shot-noise at any given signal is $G=2^{\wedge}(n_1/2)$, i.e., G equal to the square root of the dynamic range of detector 30, $DR_1$, which is $2^{\wedge}n_1$. By proper choice of the gain factor, which determines the LUT entries, system 20 will remain shot-noise limited. For this choice of gain, the full dynamic range ($DR_T$) of system 20 becomes $DR_T = G*DR_2 = 2^{\wedge}(n/2)*DR_2 = 2^{\wedge}(3n/2)$, assuming that $n_1 = n_2 = n$, with both detectors having the same dynamic range of $2^{\wedge}n/2$.

Figure 2:
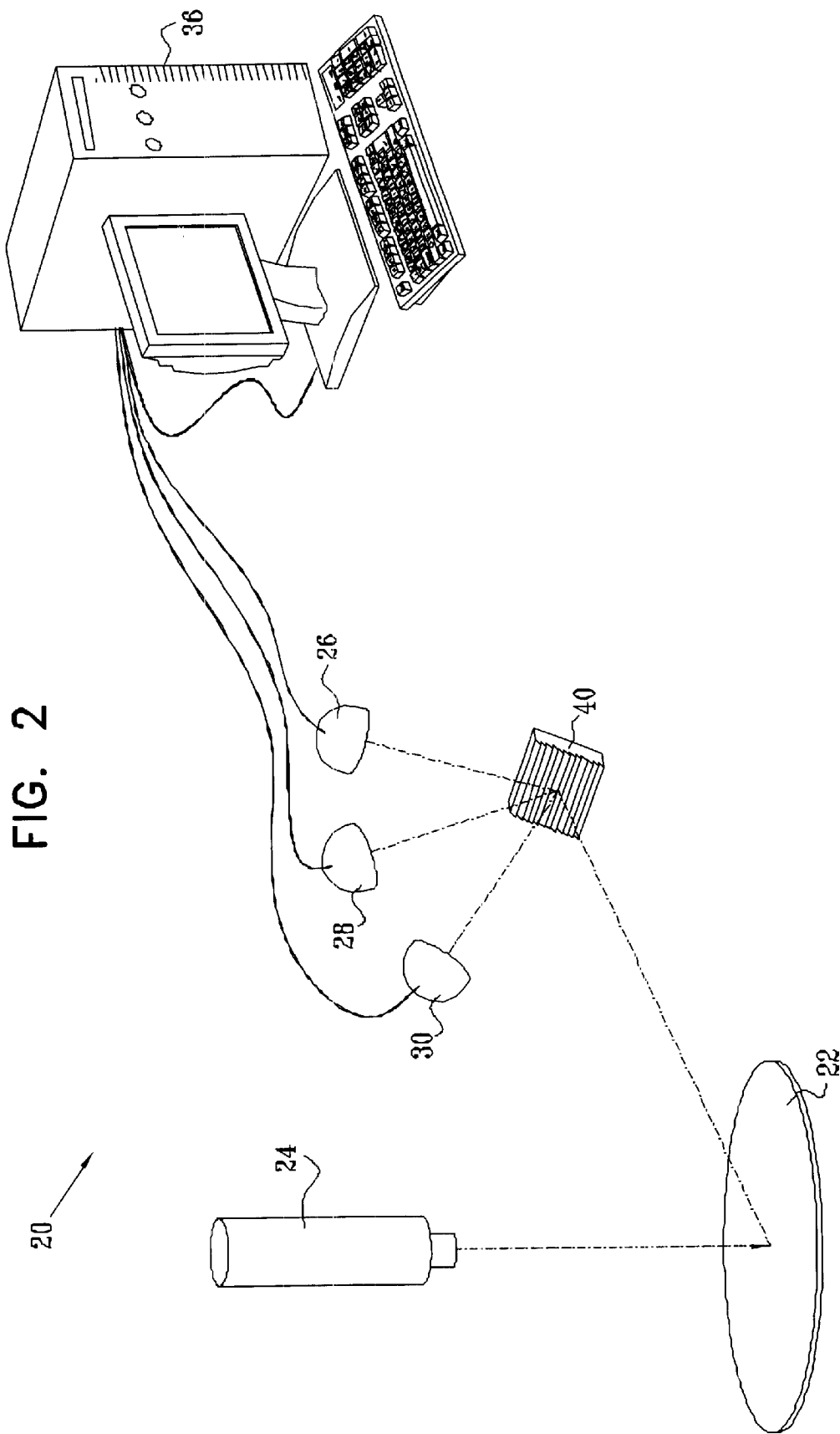

FIG. 2 is a schematic, pictorial illustration of system 20, in accordance with another preferred embodiment of the present invention. In this embodiment, a diffraction grating 40 is used in place of beamsplitter 32 to split the beam of radiation scattered from substrate 22 between detectors 26, 28 and 30. Optical elements such as lens 25 and spatial filter 38 are omitted from this figure for the sake of simplicity. Grating 40 and detectors 26, 28 and 30 are arranged so that one of the diffraction orders, such as the first order, is diffracted toward detector 30, another order, such as the second order, is diffracted toward detector 28, and still another order, such as the third order, is diffracted toward detector 26. Thus, a single optical element (grating 40) can be used to distribute the radiation among three or more detectors, in contrast to the multiple beamsplitters required in the embodiment of FIG. 1. The grating is preferably blazed so that most of the light incident on the grating is diffracted into the order that reaches detector 30, while successively smaller portions of the light are in the orders that reach detectors 28 and 26. Optionally, additional detectors may be positioned to capture other, higher orders of the grating.

Figure 3:
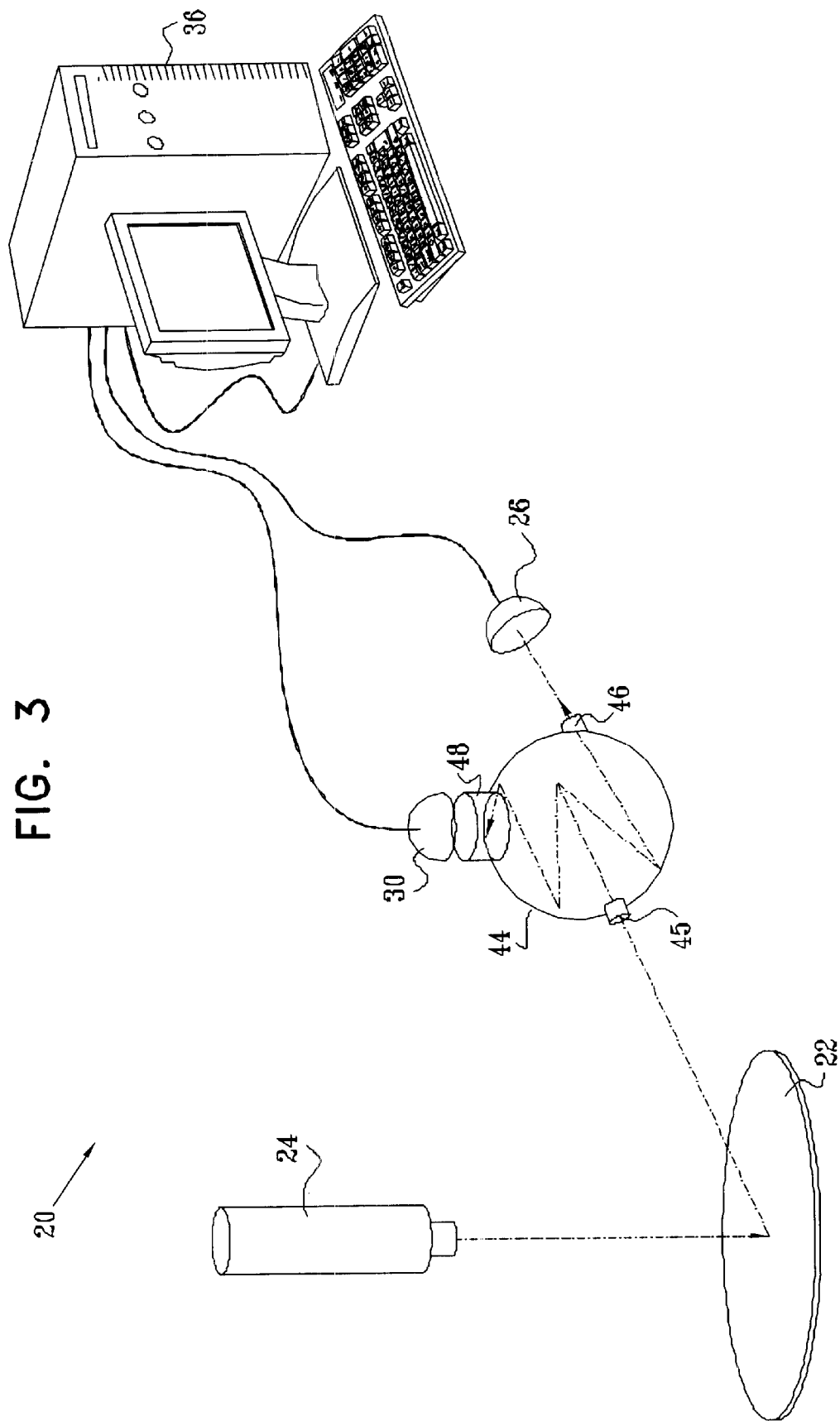

FIG. 3 is a schematic, pictorial illustration of system 20, in accordance with yet another preferred embodiment of the present invention. Light scattered from substrate 22 is collected in an integrating sphere 44 through an input port 45 of the sphere. (Here, again, some of the optical elements are omitted for the sake of simplicity.) The integrating sphere is coated internally with a diffusely-reflecting coating, as is known in the art. The light exits the integrating sphere through output ports 46 and 48, to which detectors 26 and 30 are respectively coupled. Preferably, port 48 is larger than port 46, so that high-sensitivity detector 30 receives a relatively larger share of the scattered light. An additional, intermediate port (not shown) may be provided for detector 28.

Integrating sphere 44 is advantageous in that it distributes the scattered light to the detectors in a manner that is independent of the polarization and of the scattering angle of the light (within the limits of the input aperture of the sphere). By comparison, a specularly-reflecting element such as beamsplitter 32 may be sensitive to polarization and incidence angle, leading to possible discrepancies between the signals captured by the different detectors.

FIG. 4 is a schematic, pictorial illustration of system 20, in accordance with still another preferred embodiment of the present invention. In this embodiment, an optical switch 50, such as a galvanometer mirror or acousto-optic element, switches the beam of light scattered from substrate 22 between detectors 26 and 30. The switch is preferably controlled by processor 36, based on prior knowledge of the layout of the substrate. In areas that are known to scatter strongly, switch 50 deflects the scattered light toward high-saturation detector 26, whereas in areas of weak scattering, the switch directs the light toward high-sensitivity detector 30. Additional detectors, such as intermediate detector 28, may also be added and served by switch 50.

Processor 36 combines the output signals from detectors 26 and 30 in order to produce a defect map of the entire substrate. At each point on the substrate, only the active detector signal must be processed, while the other signal can be discarded. This scheme has the advantage of reducing the burden on processor 36. It also allows system 20 to maintain a high rate of inspection throughput, since switch 50 can be scanned rapidly between the high-sensitivity and high-saturation channels. Unlike adaptive-gain systems known in the art, there is no need here to change the detector gain or other acquisition parameters on the fly.

Optionally, each of detectors 26 and 30 has its own spatial filter 52, 54, which is preferably controlled by processor 36. This configuration allows the spatial filters to be set independently in response to the different scattering characteristics of different areas of substrate 22. For example, filter 54 may be set to block diffraction lobes scattered from a certain pattern in a dim portion of the substrate, while filter 52 is set to block strong diffraction at certain azimuthal angles due to conducting lines on the substrate. Furthermore, if different spatial filtering characteristics are needed for different dim areas of the substrate, for example, processor 36 can change the characteristics of filter 54 while source 24 is scanning a bright are of the substrate, in which only filter 52 and detector 26 are used. Although loading a new filter characteristic into filter 54 is a slow process, this process does not substantially affect the throughput of system 20, since it takes place while detector 30 is idle. Filter 52 can be reloaded in like manner.

As an additional option, each of detectors 26 and 30 may have its own variable attenuator 56, 58, preferably controlled by processor 36. Attenuator 58 is particularly useful in protecting high-sensitivity detector 30 from potentially-damaging high light levels.

Although the preferred embodiments described herein relate to dark-field detection of defects on substrate 22, typically a semiconductor wafer, the principles of the present invention are similarly applicable to other types of samples and scattering measurements, and to other areas of optical inspection. In particular, the multi-detector optical schemes and processing methods of the present invention may be applied to various dark-field detection configurations and to bright-field detection, as well.

It will thus be appreciated that the preferred embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed is:

1. Apparatus for optical inspection, comprising:
    a source of optical radiation, which is adapted to scan a spot of the radiation over a sample, whereby the radiation is scattered from the spot;
    a detection system, comprising at least first and second detectors optically coupled to receive the scattered radiation and to generate respective first and second outputs responsive thereto, the detection system being configured so that the first detector detects variations in the scattered radiation with a greater sensitivity than the second detector, while the second detector saturates at a higher intensity of the scattered radiation than does the first detector; and
    a signal processor, coupled to receive the first and second outputs and to determine, responsive to the outputs, locations of defects on the sample.

2. Apparatus according to claim 1, wherein the first and second detectors have respective first and second dynamic ranges, and wherein the signal processor is adapted to process the first and second outputs so as to generate an combined output having a third dynamic range, greater than the first and second dynamic ranges, for use in determining the locations of the defects.

3. Apparatus according to claim 2, wherein the signal processor is adapted to generate the combined output as a weighted sum of the first and second outputs.

4. Apparatus according to claim 2, wherein the signal processor is adapted to generate the combined output by selecting, at each point as the spot is scanned over the sample, a value of one of the first and second outputs.

5. Apparatus according to claim 2, wherein the detection system comprises an optical switch, which is adapted to direct the scattered radiation toward either of the first and second detectors in turn, and wherein the signal processor is coupled to drive the switch so as to select, at each point as the spot is scanned over the sample, one of the detectors to which the scattered radiation is to be directed.

6. Apparatus according to claim 2, wherein the first and second detectors are characterized by respective gains, which are selected so that the sensitivity of the combined output is shot-noise limited.

7. Apparatus according to claim 1, wherein the signal processor is coupled to process each of the first and second outputs to generate respective first and second defect maps, and to combine the first and second defect maps to determine the locations of the defects on the sample.

8. Apparatus according to claim 1, wherein the first and second detectors are configured to generate the first and second outputs with respective first and second gains, relative to the intensity of the scattered radiation incident thereon, and wherein the first gain is substantially greater than the second gain.

9. Apparatus according to claim 8, wherein the first detector comprises one of a photomultiplier tube and an avalanche photodiode, while the second detector comprises a PIN photodiode.

10. Apparatus according to claim 1, wherein the detection system comprises a beamsplitter, which is positioned to split the scattered radiation between the first and second detectors.

11. Apparatus according to claim 10, wherein the beamsplitter is configured to direct a greater portion of the scattered radiation toward the first detector than toward the second detector.

12. Apparatus according to claim 1, wherein the detection system comprises a diffraction grating, which is positioned to intercept the scattered radiation and to diffract one order of the scattered radiation toward the first detector, and another order of the scattered radiation toward the second detector.

13. Apparatus according to claim 1, wherein the detection system comprises an optical element that is adapted to divide the scattered radiation between the first and second detectors in a manner that is substantially independent of a scattering angle and a polarization of the scattered radiation.

14. Apparatus according to claim 13, wherein the optical element comprises an integrating sphere, having an entrance port that is coupled to receive the scattered radiation, and first and second exit ports that are coupled to convey the scattered radiation to the first and second detectors, respectively.

15. Apparatus according to claim 14, wherein the first exit port is substantially larger than the second exit port.

16. Apparatus according to claim 1, wherein the detection system comprises at least one spatial filter, which is configured to block a portion of the scattered radiation from reaching the first and second detectors, so as to facilitate detection of the radiation that is scattered from the defects.

17. Apparatus according to claim 16, wherein the at least one spatial filter comprises first and second spatial filters, which are respectively positioned so that the first spatial filter filters the scattered radiation reaching the first detector, while the second spatial filter filters the scattered radiation reaching the second detector.

18. Apparatus according to claim 17, wherein the signal processor is coupled to independently control each of the first and second spatial filters, so as to alter the portion of the scattered radiation that is blocked by each of the spatial filters.

19. Apparatus according to claim 1, wherein the detection comprises at least one attenuator, which is controllable so as to adjust an intensity of the scattered radiation that reaches at least one of the first and second detectors.

20. Apparatus according to claim 1, and comprising a third detector, optically coupled to receive the scattered radiation and to generate a third output responsive thereto, wherein the sensitivity of the third detector is intermediate the sensitivity of the first and second detectors, and wherein the signal processor is coupled to receive the third output and to determine the locations of the defects responsive to the third output, together with the first and second outputs.

21. Apparatus according to claim 1, wherein the optical radiation comprises coherent radiation, and wherein the detection system is configured so that the detectors receive the scattered radiation in a dark-field mode.

22. Apparatus according to claim 21, wherein the sample comprises a semiconductor wafer on which a pattern is formed, and wherein the signal processor is adapted to map the locations of the defects in the pattern.

23. A method for optical inspection, comprising:
    scanning a spot of the radiation over a sample, whereby the radiation is scattered from the spot;
    configuring at least first and second detectors so that the first detector detects variations in the scattered radiation with a greater sensitivity than the second detector, while the second detector saturates at a higher intensity of the scattered radiation than does the first detector;
    detecting the scattered radiation using at least the first and second detectors so as to generate respective first and second outputs responsive thereto; and
    processing at least the first and second outputs to determine locations of defects on the sample.

24. A method according to claim 23, wherein the first and second detectors have respective first and second dynamic ranges, and wherein processing at least the first and second outputs comprises generating an combined output having a third dynamic range, greater than the first and second dynamic ranges, for use in determining the locations of the defects.

25. A method according to claim 24, wherein generating the combined output comprises computing a weighted sum of the first and second outputs.

26. A method according to claim 24, wherein generating the combined output comprises selecting, at each point as the spot is scanned over the sample, a value of one of the first and second outputs.

27. A method according to claim 24, wherein detecting the scattered radiation comprises optically switching the scattered radiation between the first and second detectors as the spot is scanned over the sample, and wherein generating the combined output comprises receiving the output from the detector to which the scattered radiation is directed.

28. A method according to claim 24, wherein the first and second detectors are characterized by respective gains, and wherein configuring at least the first and second detectors comprises setting the gains so that the sensitivity of the combined output is shot-noise limited.

29. A method according to claim 23, wherein processing at least the first and second outputs comprises processing each of the first and second outputs to generate respective first and second defect maps, and combining the first and second defect maps to determine the locations of the defects on the sample.

30. A method according to claim 23, wherein configuring at least the first and second detectors comprises configuring the detectors to generate the first and second outputs with respective first and second gains, relative to the intensity of the scattered radiation incident thereon, and wherein the first gain is substantially greater than the second gain.

31. A method according to claim 30, wherein the first detector comprises one of a photomultiplier tube and an avalanche photodiode, while the second detector comprises a PIN photodiode.

32. A method according to claim 23, wherein configuring at least the first and second detectors comprises splitting the scattered radiation between the first and second detectors.

33. A method according to claim 32, wherein splitting the scattered radiation comprises directing a greater portion of the scattered radiation toward the first detector than toward the second detector.

34. A method according to claim 32, wherein splitting the scattered radiation comprises positioning a diffraction grating to intercept the scattered radiation and to diffract one order of the scattered radiation toward the first detector, and another order of the scattered radiation toward the second detector.

35. A method according to claim 32, wherein splitting the scattered radiation comprises dividing the scattered radiation between the first and second detectors in a manner that is substantially independent of a scattering angle and a polarization of the scattered radiation.

36. A method according to claim 35, wherein dividing the scattered radiation comprises passing the scattered radiation through an integrating sphere, having first and second exit ports that are coupled to convey the scattered radiation to the first and second detectors, respectively.

37. A method according to claim 36, wherein the first exit port is substantially larger than the second exit port.

38. A method according to claim 23, wherein configuring at least the first and second detectors comprises spatially filtering the scattered radiation so as to block a portion of the scattered radiation from reaching the first and second detectors, in order to facilitate detection of the radiation that is scattered from the defects.

39. A method according to claim 38, wherein spatially filtering the scattered radiation comprises filtering the radiation using first and second spatial filters, which are respectively positioned so that the first spatial filter filters the scattered radiation reaching the first detector, while the second spatial filter filters the scattered radiation reaching the second detector.

40. A method according to claim 39, wherein filtering the radiation comprises independently controlling each of the first and second spatial filters, so as to alter the portion of the scattered radiation that is blocked by each of the spatial filters.

41. A method according to claim 23, wherein configuring at least the first and second detectors comprises variably attenuating an intensity of the scattered radiation that reaches at least one of the first and second detectors.

42. A method according to claim 23, wherein configuring at least the first and second detectors comprises configuring a third detector to receive the scattered radiation and to generate a third output responsive thereto, wherein the sensitivity of the third detector is intermediate the sensitivity of the first and second detectors, and processing at least the first and second outputs comprises processing the third output together with the first and second outputs.

43. A method according to claim 23, wherein the optical radiation comprises coherent radiation, and configuring at least the first and second detectors comprises configuring an optical system so that the detectors receive the scattered radiation in a dark-field mode.

44. A method according to claim 43, wherein the sample comprises a semiconductor wafer on which a pattern is formed, and wherein processing at least the first and second outputs comprises mapping the locations of the defects in the pattern.

\* \* \* \* \*